US011806496B2

(12) United States Patent
Vortman et al.

(10) Patent No.: US 11,806,496 B2
(45) Date of Patent: Nov. 7, 2023

(54) ADAPTIVE, CLOSED-LOOP ULTRASOUND THERAPY

(71) Applicant: INSIGHTEC, LTD., Tirat Carmel (IL)

(72) Inventors: Kobi Vortman, Haifa (IL); Yoav Levy, Hinanit (IL); Oleg Prus, Haifa (IL); Shuki Vitek, Haifa (IL)

(73) Assignee: Insightec Ltd., Tirat Carmel (IL)

( * ) Notice: Subject to any disclaimer, the term of this patent is extended or adjusted under 35 U.S.C. 154(b) by 374 days.

(21) Appl. No.: 16/771,768

(22) PCT Filed: Dec. 5, 2018

(86) PCT No.: PCT/IB2018/001603
§ 371 (c)(1),
(2) Date: Jun. 11, 2020

(87) PCT Pub. No.: WO2019/116107
PCT Pub. Date: Jun. 20, 2019

(65) Prior Publication Data
US 2021/0170204 A1 Jun. 10, 2021

Related U.S. Application Data

(60) Provisional application No. 62/597,071, filed on Dec. 11, 2017, provisional application No. 62/597,076, (Continued)

(51) Int. Cl.
*A61M 37/00* (2006.01)
*A61N 7/00* (2006.01)
*A61N 7/02* (2006.01)

(52) U.S. Cl.
CPC .......... *A61M 37/0092* (2013.01); *A61N 7/00* (2013.01); *A61N 7/02* (2013.01); *A61M 2205/50* (2013.01);
(Continued)

(58) Field of Classification Search
CPC .......... A61M 37/0092; A61M 2205/50; A61M 2230/04; A61M 2230/205; A61N 7/00;
(Continued)

(56) References Cited

U.S. PATENT DOCUMENTS 6,740,039 B1 5/2004 Rafter et al.
8,932,237 B2 1/2015 Shuki et al.
(Continued)

FOREIGN PATENT DOCUMENTS

CN 102946945 A 2/2013
CN 103842020 A 6/2014
(Continued)

OTHER PUBLICATIONS

International Search Report and Written Opinion dated Apr. 9, 2019 for corresponding International Application No. PCT/IB2018/001603 (13 pages).
(Continued)

*Primary Examiner* — Hien N Nguyen
(74) *Attorney, Agent, or Firm* — Morgan, Lewis & Bockius LLP

(57) ABSTRACT

Various approaches to focusing an ultrasound transducer includes causing the ultrasound transducer to transmit ultrasound waves to the target region; causing the detection system to indirectly measure the focusing properties; and based at least in part on the indirectly measured focusing properties, adjusting a parameter value associated with at least one of the transducer elements so as to achieve a target treatment power at the target region.

20 Claims, 12 Drawing Sheets

Related U.S. Application Data filed on Dec. 11, 2017, provisional application No. 62/597,073, filed on Dec. 11, 2017.

(52) U.S. Cl.
CPC ... *A61M 2230/04* (2013.01); *A61M 2230/205* (2013.01); *A61N 2007/0004* (2013.01); *A61N 2007/0039* (2013.01); *A61N 2007/0052* (2013.01); *A61N 2007/0056* (2013.01); *A61N 2007/0073* (2013.01); *A61N 2007/0078* (2013.01); *A61N 2007/0095* (2013.01)

(58) Field of Classification Search
CPC .............. A61N 7/02; A61N 2007/0004; A61N 2007/0039; A61N 2007/0052; A61N 2007/0056; A61N 2007/0073; A61N 2007/0078; A61N 2007/0095; A61N 2007/0086; A61B 2017/00106; A61B 2017/22007; A61B 2090/374; A61B 2090/3762; A61B 2090/378; A61B 90/37; A61B 8/481

See application file for complete search history.

(56) References Cited

U.S. PATENT DOCUMENTS

| | | | |
|---|---|---|---|
| 2003/0204141 A1 | 10/2003 | Levin et al. | |
| 2008/0269668 A1 | 10/2008 | Keenan et al. | |
| 2008/0312535 A1* | 12/2008 | Kawabata | G01S 7/52071 600/458 |
| 2009/0234231 A1 | 9/2009 | Knight et al. | |
| 2011/0270136 A1* | 11/2011 | Vitek | A61N 7/02 601/2 |
| 2012/0316439 A1 | 12/2012 | Behar | |
| 2016/0008633 A1* | 1/2016 | Vortman | A61N 7/02 601/2 |
| 2019/0151146 A1* | 5/2019 | Kim | A61F 9/008 |

FOREIGN PATENT DOCUMENTS

| | | |
|---|---|---|
| WO | WO2011/025893 A1 | 3/2011 |
| WO | WO2011/034892 A2 | 3/2011 |
| WO | WO2013/046076 A1 | 4/2013 |
| WO | 2014/135987 | 9/2014 |

OTHER PUBLICATIONS

International Preliminary Report on Patentability dated Jun. 16, 2020 for International Application No. PCT/IB2018/001603, 7 pgs.
International Search Report and Written Opinion dated Mar. 18, 2019 for International Application No. PCT/IB2018/001548, 11 pgs.
International Preliminary Report on Patentability dated Jun. 16, 2020 for International Application No. PCT/IB2018/001548, 7 pgs.
International Search Report and Written Opinion dated Jun. 4, 2019 for International Application No. PCT/IB2018/001537, 18 pgs.
First Office Action, CN201880089076.2, dated Sep. 24, 2021, 12 pgs.
First Office Action, CN201880088970.8, dated Sep. 16, 2021, 15 pgs.
First Office Action, CN201880087835.1, dated Nov. 11, 2021, 22 pgs.
Insightec Ltd., Communication Pursuant to Article 94(3), EP18852736.0, dated Mar. 30, 2022, 4 pgs.
Insightec Ltd., Communication Pursuant to Article 94(3), EP18845443.3, dated Mar. 29, 2022, 4 pgs.
Insightec Ltd., Communication Intention to Grant EP Patent, EP18842722.3, dated Feb. 11, 2022, 8 pgs.
Priscilla Lai et al., Breast tumor response to ultrasound mediated excitation of microbubles and radiation therapy in vivo, Oncoscience, Advance Publications 2016, Mar. 24, 2016 (Year: 2016), 11 pgs.
Ine Lentacker, Design and Evaluation of Doxorubicin-containing Microbubles for Ultrasound-triggered Doxorubicin Delivery: Cytotoxicity and Mechanisms Involved, Molecular Therapy, Jan. 2010: vol. 18 No. 1, 101-108, Epub Jul. 21, 2009 (Year: 2009), 8 pgs.
Levy, Office Action, U.S. Appl. No. 16/771,770, dated Aug. 10, 2022, 16 pgs.
Japanese Notice of Reason for Rejection, dated Jul. 29, 2022 for JP Patent Application No. 2020-531576.

* cited by examiner

ADAPTIVE, CLOSED-LOOP ULTRASOUND THERAPY

CROSS-REFERENCE TO RELATED APPLICATION

This application is a U.S. National Phase Application of PCT/IB2018/001603, filed Dec. 5, 2018, which claims the benefit of and priority to U.S. Provisional Patent Applications Nos. 62/597,071, 62/597,076 and 62/597,073 (all filed on Dec. 11, 2017). The entire disclosures of these priority documents are hereby incorporated by reference.

TECHNICAL FIELD

The present invention relates, in general, to ultrasound therapy, and, in particular, to systems and methods for measuring focusing properties of ultrasound beams and, based thereon, adjusting parameters of the ultrasound in order to optimize focusing properties.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, targeted drug delivery, disruption of the blood-brain barrier (BBB), lysing of clots, and other medical procedures. During treatment, a piezoceramic transducer is placed externally to the patient, but in close proximity to a target region to be treated. The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target region. Alternatively or additionally, a single transducer may be formed of a plurality of individually driven transducer elements whose phases and/or amplitudes can each be controlled independently. Such a "phased-array" transducer facilitates steering the focal zone to different locations by adjusting the relative phases among the transducers. As used herein, the term "element" means either an individual transducer in an array or an independently drivable portion of a single transducer.

As acoustic energy passes through tissue, it may interact with the tissue through multiple processes, including propagation, scattering, absorption, reflection, and refraction. The intensity of the acoustic energy reaching the target region generally determines the therapeutic effectiveness of the treatment, i.e., the volume of tissue destroyed in the vicinity of the focal zone. The size of the focal zone may also depend upon system parameters such as transducer element characteristics, frequency of the acoustic energy, and focal depth (the distance from the transducer to the focal zone), as well as patient-related parameters, such as tissue inhomogeneity.

When a transducer is activated, the relative phases of drive signals delivered to each transducer element may be adjusted based on the distance of each transducer element from the focal zone. Generally, an average speed of sound is used to approximate the speed at which the acoustic energy passes through tissue and to predict the location of the focal zone.

While system parameters are generally fixed for a given transducer array, tissue homogeneity may vary significantly from patient to patient, and even between different tissue regions within the same patient and organ. Tissue inhomogeneity may decrease the intensity of the acoustic energy reaching the focal zone and may even move the location of the focal zone within the patient's body. Specifically, because the speed of sound differs in different types of tissue, as portions of a beam of acoustic energy travel along different paths having different tissue types in the beam path, they may experience different speeds of sound, which shift the relative phases of acoustic energy transmitted from respective transducer elements. This phase shifting may decrease the constructive interference of the acoustic energy at the focal zone, thereby reducing the effectiveness of the treatment, or may even move the focal zone in an unpredictable manner.

Tissue inhomogeneity may also cause refraction of acoustic energy at the boundaries of tissue regions having different speeds of sound. Refraction may decrease constructive interference, and hence, the intensity of the acoustic energy at the focal zone, particularly when the acoustic energy passes through bone. The distorted focus and reduced acoustic intensity may significantly affect treatment efficiency and efficacy at the target.

Accordingly, there is a need for an approach that measures focusing properties at the target region of a particular patient and adjusts parameters of the ultrasound transducer to optimize the focusing properties, thereby maximizing the amount of acoustic energy available at the focus.

SUMMARY

Various embodiments of the present invention provide systems and methods for measuring ultrasound focusing properties (e.g., acoustic power or peak acoustic intensity) at the target region in real time during a treatment procedure and, based thereon, adjusting one or more parameters (e.g., amplitudes, frequencies and/or phase shifts) of the transducer elements in order to achieve one or more desired focusing properties. The focusing properties may be indirectly measured using any suitable approach. For example, in one embodiment, acoustic radiation force impulse (ARFI) imaging is employed to measure tissue displacement resulting from the acoustic pressure at the target region during treatment; the tissue displacement correlates with the amount of energy concentrated at the measured region and, therefore, the quality of the focus. Alternatively, acoustic pressure (which also correlates with delivered acoustic energy) may be indirectly measured using acoustic signals from the target region. For example, during treatment, small gas bubbles ("microbubbles") may be generated within and/or introduced into the target region. The microbubbles may act as ultrasound reflectors. Alternatively, other exogenous agents may be introduced and these may act as reflectors (see, e.g., http://tinyurl.com/y7ug73lr) or become converted in the body into reflectors (e.g., ultrasound-triggered phase transition nanodroplets—see, e.g., http://tinyurl.com/yc8ommz5). By analyzing information (e.g., power, amplitude and/or the shape of the spectrum) characterizing the reflections from the microbubbles, the acoustic pressure at the target regions (and, thereby, the energy concentration) can be estimated. In various embodiments, based on the measured acoustic pressure (using ARFI, microbubble reflections or any suitable approach), the transducer parameters (e.g., phase shifts, frequencies and/or amplitudes) can be adjusted. These adjustments may be repeated until the detected ARFI signals or microbubble reflection signals are consistent with a desired focus property as indicated by a corresponding acoustic pressure. As used herein, the terms "indirectly measured" or "indirect measurements" refer to measurements of a parameter value that is not a focusing property (e.g., the acoustic power or peak intensity in the focus); rather, the measured parameter value is a function of the focusing properties and thus, based on the measurements of the parameter value, the focusing properties can be inferred.

Additionally or alternatively, acoustic signals reflected from the target may be measured by different transducer regions and/or multiple acoustic-signal detectors, each associated with a different transducer region. The relative amplitudes of the reflected signals received by these transducer regions (or acoustic-signal detectors) may reveal the relative contributions of the energy at the target region 101 from the respective regions of the transducer. Based on this information, the parameter values associated with the transducer regions may be adjusted so as to improve the focusing properties and/or shape the acoustic beam at the target. For example, the output amplitudes of transducer regions found to contribute energy intensities at the target that fall below expectations may be increased to compensate for the energy lost, for example, along their beam paths. In addition, by adjusting the amplitude apodization and/or phases associated with the transducer elements, the focus may be shaped to conform to a specific target shape. The focus shaping may be based on the reflection signals from the target and/or an acoustic simulation.

Generally, as noted, the acoustic effect generated at the target region positively correlates with the peak acoustic intensity in that region, and with the energy absorption of the target tissue. In addition, higher absorption occurs at a higher frequency. On the other hand, the acoustic losses in beam intensity on the way to the target are positively correlated with the frequency. In order to maximize the delivered acoustic energy at the target, it may be desirable to select an optimal ultrasound frequency (accounting for the value of the absorption coefficient at that frequency in both the beam path and at the target) for providing maximal energy deposit at the target. In various embodiments, this is achieved by iteratively setting a test frequency sonicating the target and using ARFI to directly measure acoustic effects or, alternatively, by using reflections from the microbubbles to measure the acoustic pressure generated at the target. Based on the measured acoustic pressure and its corresponding test frequency, the frequency-dependent absorption coefficient can be computed or estimated. In one embodiment, the optimal frequency that maximizes the energy absorbed at the target region can then be determined based at least in part on the computed absorption coefficient. Alternatively, the test frequency corresponding to the maximal acoustic pressure may be selected as the optimal frequency. During treatment, the ultrasound transducer may be activated in accordance with the determined optimal frequency to treat the target.

While the frequency selected as optimal may maximize the energy absorbed at the target region, it may also deliver energy to surrounding non-target tissue beyond a tolerable level, thereby resulting in undesired damage to the non-target tissue. Therefore, it may be preferable to apply sonications having a frequency corresponding to a smaller absorption coefficient (compared to that of the optimal frequency) so as to avoid damage to the non-target tissue, thereby trading off reduced energy absorption at the target region for greater clinical safety. In one implementation, when the energy absorption at the target falls below that needed to produce a minimally acceptable treatment efficiency, microbubbles may be introduced and/or generated at the target region to enhance ultrasound treatment effects.

Accordingly, in one aspect, the invention pertains to a system for focusing an ultrasound transducer. In various embodiments, the system includes an ultrasound transducer having multiple transducer elements; a detection system for indirectly measuring a focusing property (e.g., an acoustic pressure and/or a peak acoustic intensity) at a target region; and a controller. In one implementation, the controller is configured to (a) cause the ultrasound transducer to transmit ultrasound waves to the target region; (b) cause the detection system to indirectly measure the focusing property; and (c) based at least in part on the indirectly measured focusing property, adjust a parameter value (e.g., a frequency, a phase, a power level, or an amplitude) associated with one or more transducer elements so as to achieve a target treatment power at the target region.

In addition, the detection system may be further configured to measure the acoustic pressure and/or peak acoustic intensity at a non-target region; the controller is further configured to adjust the parameter value associated with the transducer element(s) so as to avoid damage to the non-target tissue. In various embodiments, the controller is further configured to (d) transmit second ultrasound waves, based on the adjusted parameter value, to the target region; and (e) repeat steps (b), (c), (d) until a stopping condition is satisfied. The stopping condition may be, for example, a difference between the currently measured focusing property and previously measured focusing property being below a threshold and/or a number of iterations exceeding a predetermined limit.

The detection system may include an ARFI imaging system and/or an acoustic-signal detector. In addition, the system may further include an administration device for introducing an exogenous agent or microbubbles to the target region. The controller may then be further configured to cause the acoustic-signal detector to measure acoustic signals from the exogenous agent or microbubbles. In one embodiment, the controller is further configured to determine the focusing property based at least in part on a value (e.g., an amplitude, a power, a wave pattern and/or a spectral signature) associated with the measured acoustic signals. Additionally, the controller may be further configured to establish a relationship between the value associated with the measured acoustic signals and the focusing property and determine the focusing property based at least in part on the relationship. In some embodiments, the controller is further configured to adjust the parameter value to (i) cause cavitation of the microbubbles, and (ii) cause the microbubbles, during cavitation, to behave as half-wavelength or quarter-wavelength rigid-sphere reflectors. In addition, the controller may be further configured to cause at least some of the transducer elements to measure acoustic signals from the exogenous agent or microbubbles. Further the controller may be further configured to compare a measured treatment power associated with the indirectly measured focusing property to a predetermined value; and upon determining that the measured treatment power is smaller than the predetermined value, cause the administration device to introduce an exogenous agent or microbubbles to the target region.

The detection system may indirectly measure the focusing property at two or more regions of the transducer elements; the controller may then be further configured to adjust the parameter value based at least in part on the measurements at the two or more regions of the transducer elements. For example, the detection system may include two or more acoustic-signal detectors for measuring intensities of acoustic signals from the target region at the two or more regions of the transducer elements, and the controller is further configured to adjust the power levels associated with the two or more regions of the transducer elements based at least in part on the measured intensities of the acoustic signals. In various embodiments, the controller is further configured to adjust the power levels associated with the two or more regions of the transducer elements so as to compensate for a difference between the intensities of acoustic signals measured at the two or more regions of the transducer elements. Additionally or alternatively, the controller may be further configured to adjust the parameter value associated with the transducer element(s) based on an acoustic simulation. The controller may be further configured to adjust the parameter value associated with the transducer element(s) so as to shape an acoustic beam at the target region. In one embodiment, the controller is further configured to determine energy absorption of tissue at the target region based at least in part on the indirectly measured focusing property. The controller may then be further configured to determine the frequency based at least in part on the energy absorption.

In another aspect, the invention relates to a method of focusing an ultrasound transducer having multiple transducer elements. In various embodiments, the method includes (a) causing the ultrasound transducer to transmit ultrasound waves to a target region; (b) indirectly measuring a focusing property (e.g., an acoustic pressure and/or a peak acoustic intensity) at the target region; and (c) based at least in part on the indirectly measured focusing property, adjusting a parameter value (e.g., a frequency, a phase, a power level, or an amplitude) associated with one or more transducer elements so as to achieve a target treatment power at the target region.

In addition, the method may further include measuring the acoustic pressure and/or peak acoustic intensity at a non-target region; and adjusting the parameter value associated with the transducer element(s) so as to avoid damage to the non-target tissue. In various embodiments, the method further includes (d) transmitting second ultrasound waves, based on the adjusted parameter value, to the target region; and (e) repeating steps (b), (c), (d) until a stopping condition is satisfied. The stopping condition may be, for example, a difference between the currently measured focusing property and previously measured focusing property being below a threshold and/or a number of iterations exceeding a predetermined limit.

The focusing property may be indirectly measured using an ARFI imaging system and/or an acoustic-signal detector. In addition, the method may further include introducing an exogenous agent or microbubbles to the target region. The method may then include measuring acoustic signals from the introduced exogenous agent or microbubbles. In addition, the method may further include determining the focusing property based at least in part on a value (e.g., an amplitude, a power, a wave pattern or a spectral signature) associated with the measured acoustic signals. In one embodiment, the method further includes establishing a relationship between the value associated with the measured acoustic signals and the focusing property; and determining the focusing property based at least in part on the relationship. In some embodiments, the method further includes adjusting the parameter value to (i) cause cavitation of the microbubbles, and (ii) cause the microbubbles, during cavitation, to behave as half-wavelength or quarter-wavelength rigid-sphere reflectors. Additionally, the method may further include causing at least some of the transducer elements to measure acoustic signals from the introduced exogenous agent or microbubbles. Further, the method may include comparing a measured treatment power associated with the indirectly measured focusing property to a predetermined value; and upon determining that the measured treatment power is smaller than the predetermined value, causing the administration device to introduce an exogenous agent or microbubbles to the target region.

In various embodiments, the method further includes indirectly measuring the focusing property at two or more regions of the transducer elements; and adjusting the parameter value based at least in part on the measurements at the two or more regions of the transducer elements. For example, the method may further include measuring intensities of acoustic signals from the target region at the two or more regions of the transducer elements, and adjusting the power levels associated with the two or more regions of the transducer elements based at least in part on the measured intensities of the acoustic signals. In one implementation, the method further includes adjusting the power levels associated with the two or more regions of the transducer elements so as to compensate for a difference between the intensities of acoustic signals measured at the two or more regions of the transducer elements. Additionally or alternatively, the method may further include adjusting the parameter value associated with the transducer element(s) based on an acoustic simulation. The method may further include adjusting the parameter value associated with the transducer element(s) so as to shape an acoustic beam at the target region. In one embodiment, the method further includes determining energy absorption of tissue at the target region based at least in part on the indirectly measured focusing property. The method may then include determining the frequency based at least in part on the energy absorption.

Another aspect of the invention relates to a system for focusing an ultrasound transducer. In various embodiments, the system includes an ultrasound transducer having multiple subsets of transducer elements, each of the subsets having different spatial arrangements with respect to a target region; a detection system for measuring a focusing property at the target region; and a controller. In one implementation, the controller is configured to cause two or more subsets of the transducer elements to transmit ultrasound waves to the target region; cause the detection system to indirectly measure the focusing property; and based at least in part on the indirectly measured focusing property, adjust a parameter value (e.g., a transmitting power) associated with one or more subsets of the transducer elements so as to achieve a target treatment power at the target region. The detection system may be further configured to measure an acoustic pressure and/or a peak acoustic intensity at a non-target region; the controller may then be further configured to adjust a frequency and/or a transmitting power associated with the subset(s) of the transducer elements so as to avoid damage to the non-target tissue.

In yet another aspect, the invention pertains to a method for focusing an ultrasound transducer having multiple subsets of transducer elements, each of the subsets having different spatial arrangements with respect to a target region. In various embodiments, the method includes causing two or more subsets of the transducer elements to transmit ultrasound waves to the target region; indirectly measuring a focusing property at the target region; and based at least in part on the indirectly measured focusing property, adjusting a parameter value (e.g., a transmitting power) associated with one or more subsets of the transducer elements so as to achieve a target treatment power at the target region. The method may further include measuring an acoustic pressure and/or a peak acoustic intensity at a non-target region; and adjusting a frequency and/or a transmitting power associated with the subset(s) of the transducer elements so as to avoid damage to the non-target tissue.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
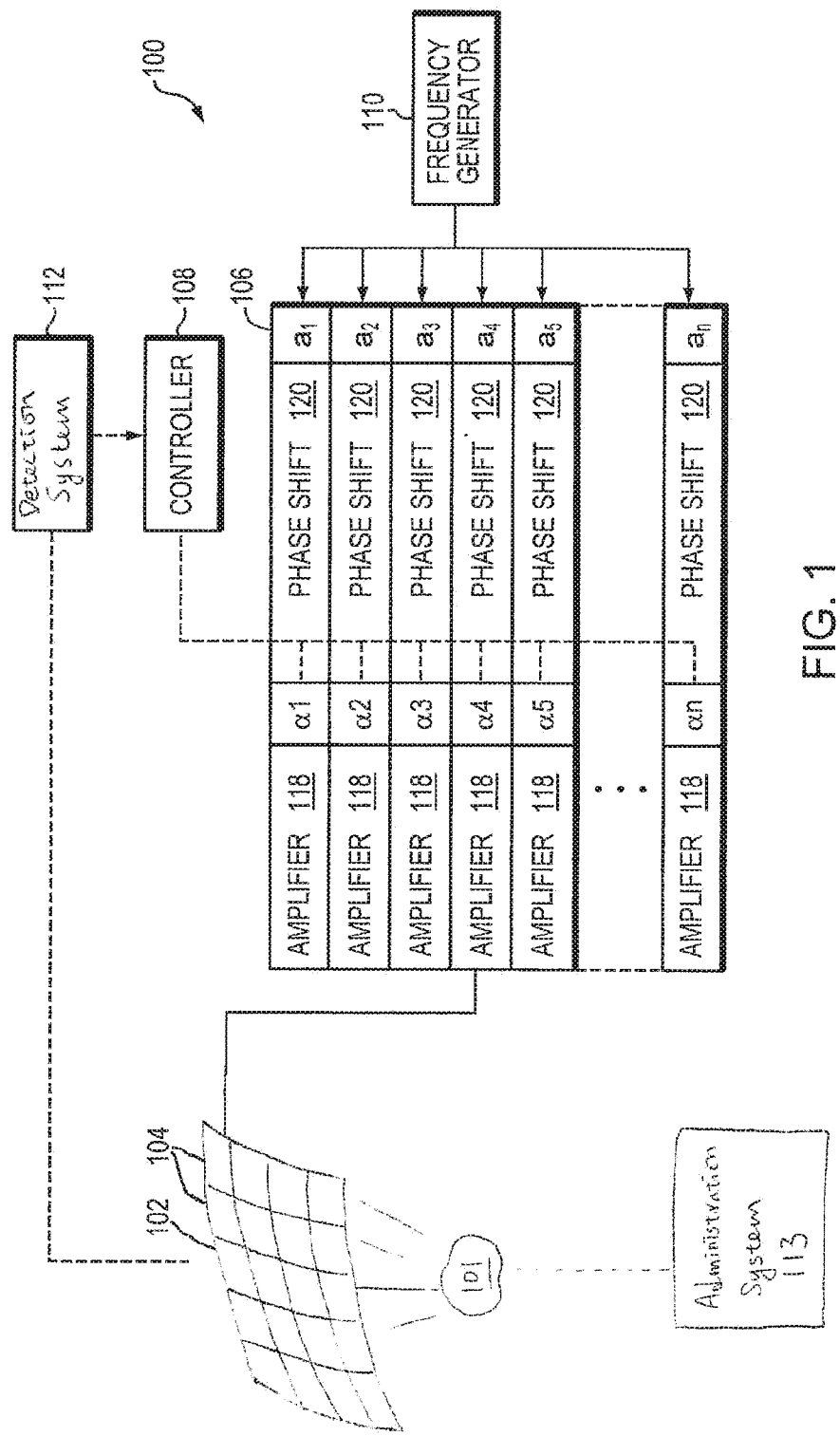
FIG. 1 illustrates a focused ultrasound system in accordance with various embodiments.

FIG. 1 illustrates an exemplary ultrasound system 100 for generating and delivering a focused acoustic energy beam to a target region 101 within a patient's body. The illustrated system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes a detection system 112 for measuring information about the focus at the target region 101 and an administration system 113 for introducing an exogenous agent (including, for example, emulsion and/or a droplets composed of various liquid perfluorocarbon agents) and/or microbubbles into the patient's body as further described below.

The array 102 may have a curved (e.g., spherical or parabolic) or other contoured shape suitable for placement on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezocomposite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the intervening tissue located between the transducer elements 104 and the target region onto the target region 101, and account for wave distortions induced in the intervening tissue. The amplification factors and phase shifts are computed using the controller 108, which may provide the computational functions through software, hardware, firmware, hardwiring, or any combination thereof. In various embodiments, the controller 108 utilizes a general-purpose or special-purpose digital data processor programmed with software in a conventional manner, and without undue experimentation, in order to determine the phase shifts and amplification factors necessary to obtain a desired focus or any other desired spatial field patterns.

To confirm the location and measure the properties of the focus, in various embodiments, the detection system 112 includes or consists of an ARFI imaging system. Because ARFI generally requires lower ultrasound energies during alignment and calibration procedures than other methods, and the ultrasound intensity preceding the actual treatment is preferably minimized to avoid damage to tissue outside the target, ARFI is typically preferred. In one implementation, the ARFI imaging system is magnetic-resonance based (i.e., MR-ARFI). Typically, in MR-ARFI, the ultrasound transducer 102 is driven so as to focus an ultrasound wave/pulse into the body at or near the target region 101. The ultrasound wave exerts acoustic radiation force onto the material along its path. At the focus, where the waves converge, this pressure is highest, resulting in a temporary local displacement of the material in the longitudinal direction and/or in shear waves that propagate radially away from the focus. Thus, the ultrasound pressure creates a displacement field that directly corresponds to the acoustic field. The displacement field may then be visualized by an MRI apparatus.

Figure 2:
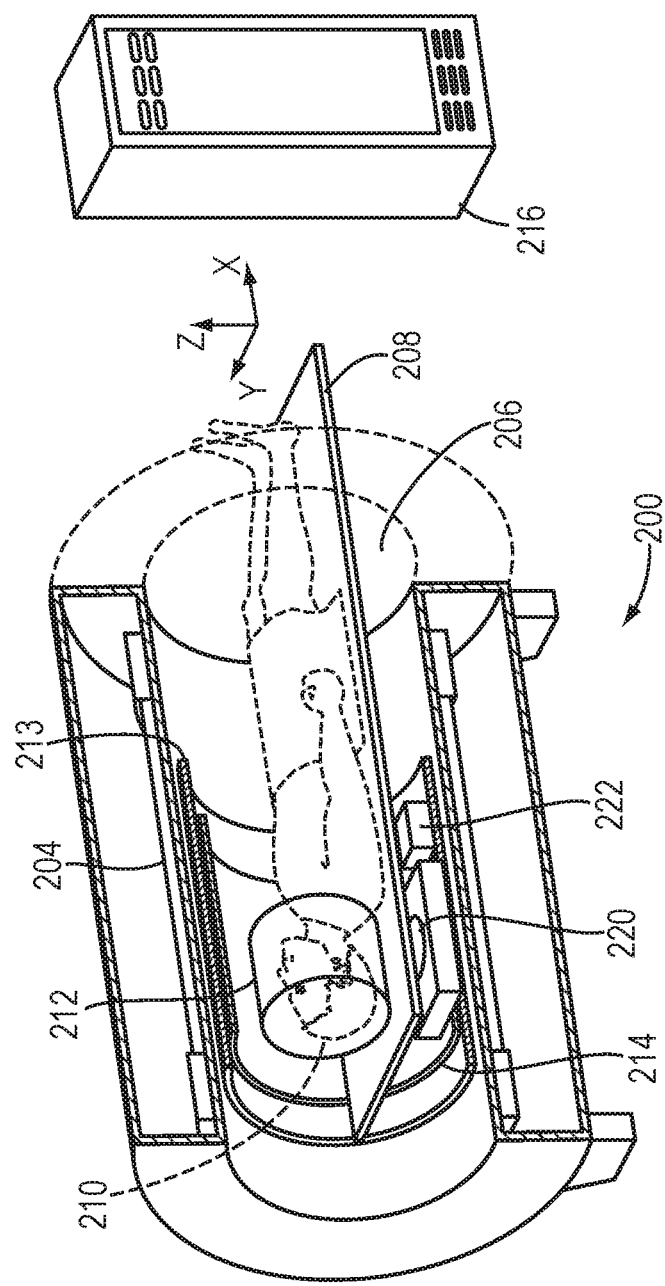
FIG. 2 illustrates an exemplary MRI apparatus in accordance with various embodiments of the present invention.

FIG. 2 depicts an exemplary MRI apparatus 200 including a cylindrical electromagnet 204, which generates the requisite static magnetic field within a bore 206 of the electromagnet 204. During medical procedures, a patient is placed inside the bore 206 on a movable support cradle 208. A region of interest 210 (e.g., the patient's head) may be positioned within an imaging region 212 in which the electromagnet 204 generates a substantially homogeneous field. A set of cylindrical magnet field gradient coils 213 may also be provided within the bore 206 and surrounding the patient. The gradient coils 213 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 214 surrounding the imaging region 212 emits RF pulses into the imaging region 212, and receives MR response signals emitted from the region of interest 210. (Alternatively, separate MR transmitter and receiver coils may be used.)

The MRI apparatus 200 generally includes an MRI controller 216 that controls the pulse sequence, i.e., the relative timing and strengths of the magnetic field gradients and the RF excitation pulses and response detection periods. The MRI controller 216 may be combined with the transducer controller 108 into an integrated system control facility.

The MR response signals are amplified, conditioned, and digitized into raw data using a conventional image-processing system, and further transformed into arrays of image data by conventional methods known to those of ordinary skill in the art. The image-processing system may be part of the MRI controller 216, or may be a separate device (e.g., a general-purpose computer containing image-processing software) in communication with the MRI controller 216 and/or the transducer controller 108.

In various embodiment, the gradient coils 213 apply transient-motion or displacement-sensitizing magnetic field gradients to the imaging region 212 for visualizing the displacement field of the material created by the ultrasound pressure. When the ultrasound pulse is applied in the presence of such gradients, the resulting displacement is directly encoded into the phase of the MR response signal. For example, the gradient coils 213 and transducer 102 may be configured such that the ultrasound pulse pushes material near the focus toward regions of the magnetic field with higher field strengths. In response to the resulting change in the magnetic field, the phase of the MR response signal changes proportionally, thereby encoding in the signal the displacement caused by the ultrasound radiation force. In general, the stronger the acoustic force, the greater will be the maximum displacement at the center of the focus. This relationship may be exploited to adjust the transducer elements so as to achieve a desired pressure at the focus as further described below. Further details about MR-ARFI is provided in U.S. Pat. No. 8,932,237 and U.S. Patent Publication No. 2013/0150756, the entire disclosures of which are hereby incorporated herein by reference.

Alternatively or additionally, the detection system 112 may include an acoustic-signal detector (e.g., a hydrophone) for measuring acoustic signals reflected from the target region 101; the reflection signals may provide information (such as the acoustic pressure or peak intensity) about the target region 101. Accordingly, the acoustic-signal detector may indirectly monitor the focusing properties at the target in real time during treatment. In one embodiment, the transducer elements 104 possess both transmit and receive capabilities. Thus, at least some of the transducer elements may be configured to measure acoustic signals from the target region 101. Approaches to configuring the transducer elements 104 for detecting the reflected signals are provided, for example, in the U.S. Patent Application No. 62/861,282, the contents of which are incorporated herein by reference.

In various embodiments, the acoustic energy emitted by the transducer elements 104 may be above a threshold and thereby cause generation of a bubble or a small cloud of gas bubbles (or "microbubbles") in the liquid contained in the tissue. Because of their encapsulation of gas therein, the microbubbles act as reflectors of ultrasound. Additionally or alternatively, the microbubbles (and/or an exogenous agent) may be introduced, via the administration system 113, into the target region 101 so as to provide stronger reflection signals from the target. Depending upon the amplitude and frequency of the applied acoustic field, the microbubbles may oscillate, stream and/or collapse. Accordingly, in various embodiments, the ultrasound parameters (e.g., amplitudes and/or frequencies associated with the transducer elements) may be adjusted such that the microbubbles, during cavitation, generate a local discontinuity in the medium and behave as half-wavelength (or, in some embodiments, quarter-wavelength) rigid-sphere reflectors. Amplitudes of the signals from the exploding microbubbles may be directly related to the local peak acoustic intensities and independent from detailed microstructures of the cavitation events. Accordingly, by detecting the amplitudes or powers of signals from the microbubble explosion, the focusing properties (e.g., the acoustic power or peak intensity) at the target region 101 can be obtained or estimated. Approaches to generating the microbubbles and/or introducing them into the target region 101 are provided, for example, in U.S. patent application Ser. Nos. 15/708,214, 15/837,392 and 62/597,073, International Application No. PCT/IB2017/000990, and International patent Applications entitled "Controlling Delivery of Therapeutic Agent in Microbubble-Enhanced Ultrasound Procedures" and "Control of Exogenous Agent Characteristics in Microbubble-Mediated Ultrasound Procedures" filed on even date herewith, the contents of which are incorporated herein by reference.

Figure 3A:
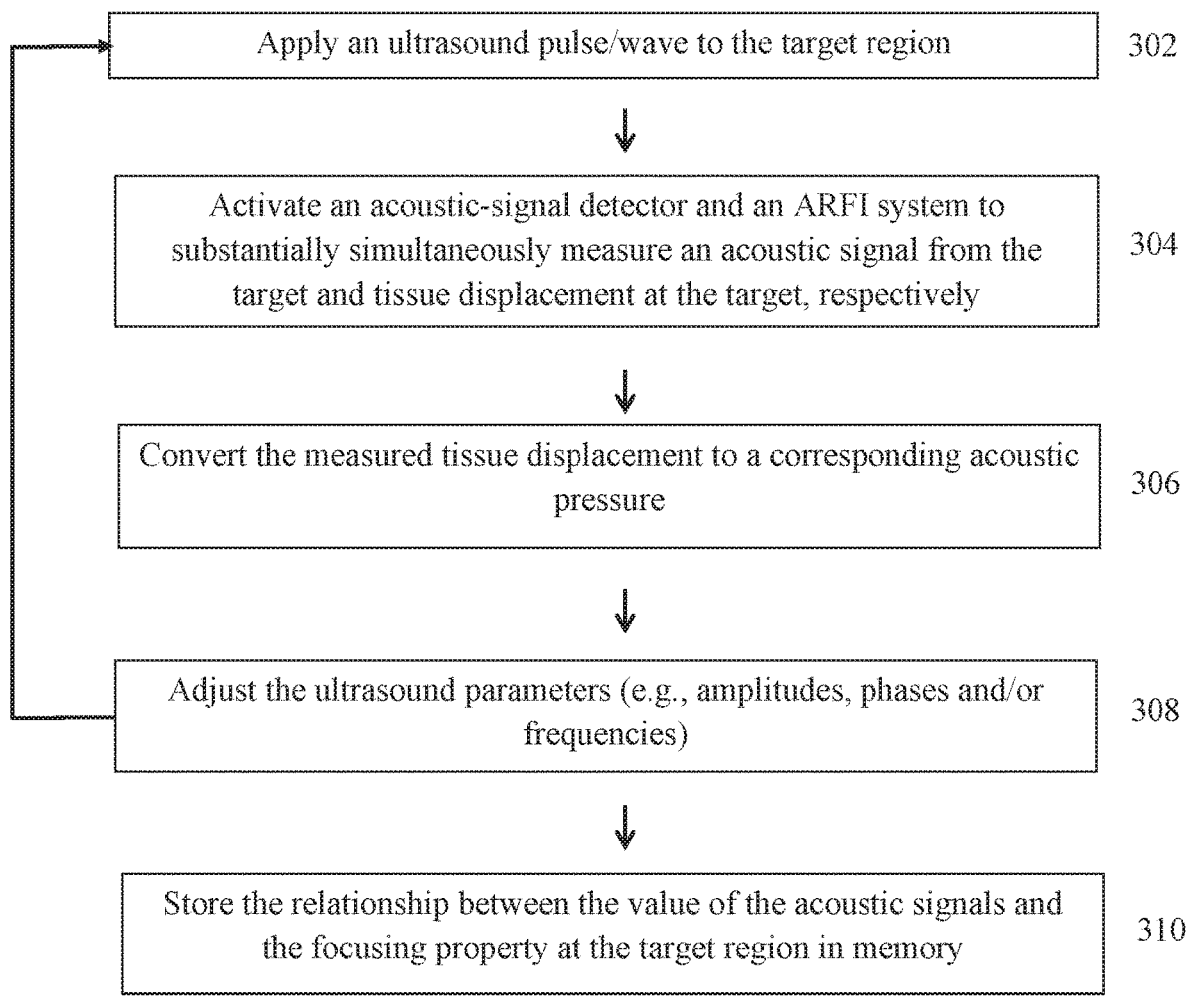
FIG. 3A is a flow chart illustrating an approach for establishing a relationship between a parameter value of detected acoustic signals from the target region and the corresponding focusing properties at the target region in accordance with various embodiments of the present invention.
Figure 3B:
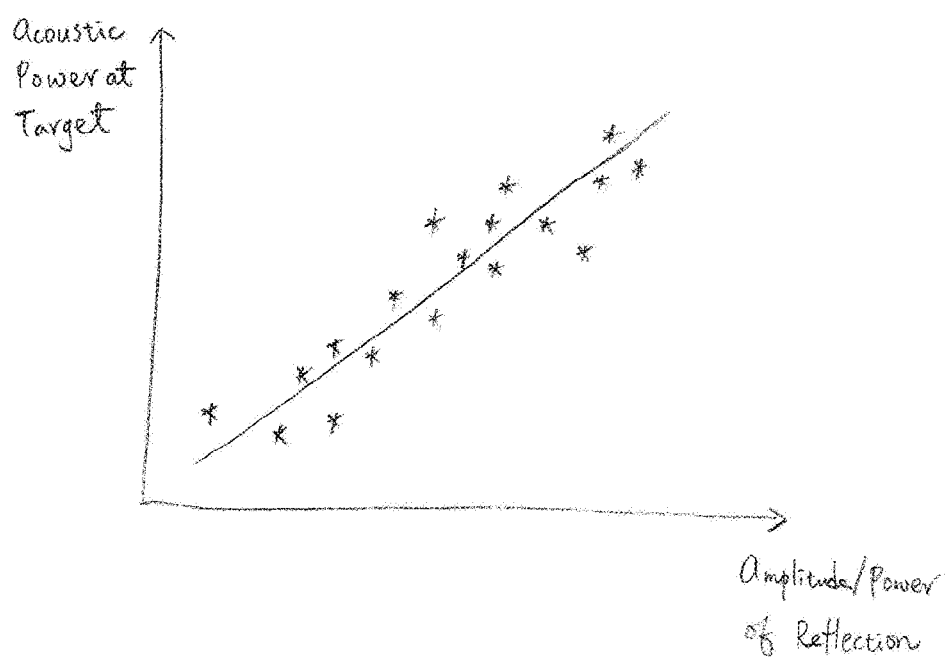
FIG. 3B depicts an exemplary relationship between a parameter value of acoustic signals from the target region and the corresponding focusing properties at the target region in accordance with various embodiments of the present invention.

In various embodiments, a relationship between the value of a parameter (e.g., the power or amplitude) of the detected acoustic signals and one or more focusing properties (e.g., the acoustic power or peak acoustic intensity) at the target region is established prior to or during ultrasound treatment. In one implementation, the relationship is established based on measurements from previous treatment(s) on the same or a different patient, averaged across patients, or ex-vivo laboratory experiments. FIG. 3A depicts an exemplary approach 300 for establishing the relationship at the beginning of the treatment using the acoustic-signal detector (or ultrasound transducer) in conjunction with the ARFI system in accordance herewith. In a first step 302, the transducer elements may apply an ultrasound pulse/wave to the target region. Parameter values (e.g., amplitudes, phases, and/or frequencies) associated with the transducer elements may be estimated empirically and/or using a physical model so as to generate a focus at the target region as described above. In a second step 304, upon application of the ultrasound wave, the acoustic-signal detector 112 and ARFI system may be activated to substantially simultaneously measure an acoustic signal from the target and tissue displacement at the target, respectively. In a third step 306, the measured tissue displacement is then converted to a corresponding acoustic pressure based on a known relationship, which may be established empirically based on a series of measurements or acquired from the literature. In a fourth step 308, the ultrasound parameters (e.g., amplitudes, phases, or frequencies) can then be adjusted. The transducer elements may then be activated based on the adjusted parameter values, and the acoustic signal and tissue displacement in response to the adjusted parameter values are measured. In various embodiments, steps 302-308 are repeated until sufficient data has been acquired to reliably establish the relationship between the value of the acoustic signals and the focusing properties at the target region 101 (as depicted in FIG. 3B). The relationship may then be stored in memory accessible to the controller 108 (in step 310).

Figure 4A:
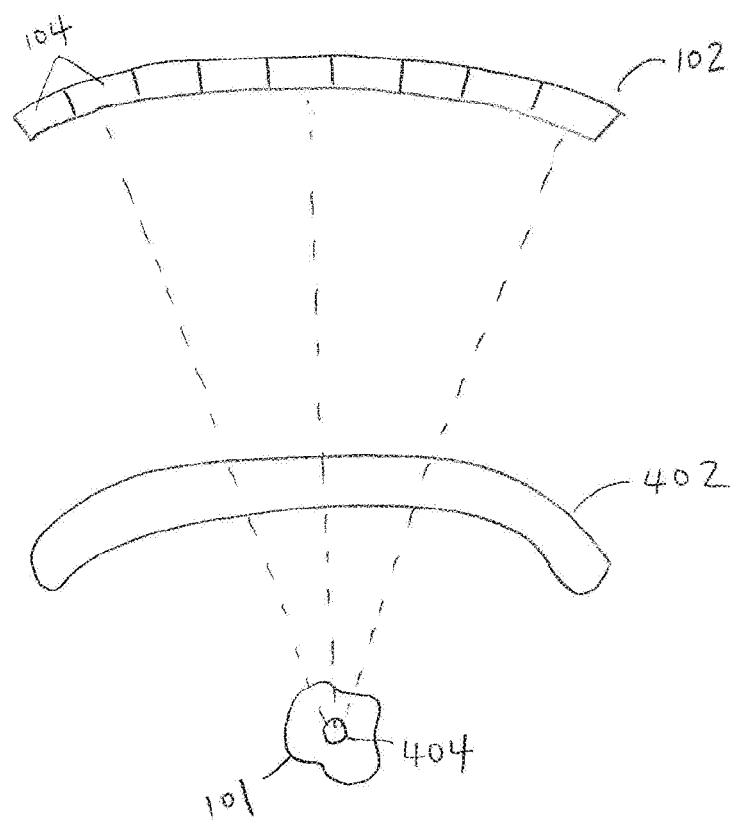
FIG. 4A illustrates an implementation of a 3D skull replica or an ex-vivo skull in a focused ultrasound system in accordance with various embodiments.
Figure 4B:
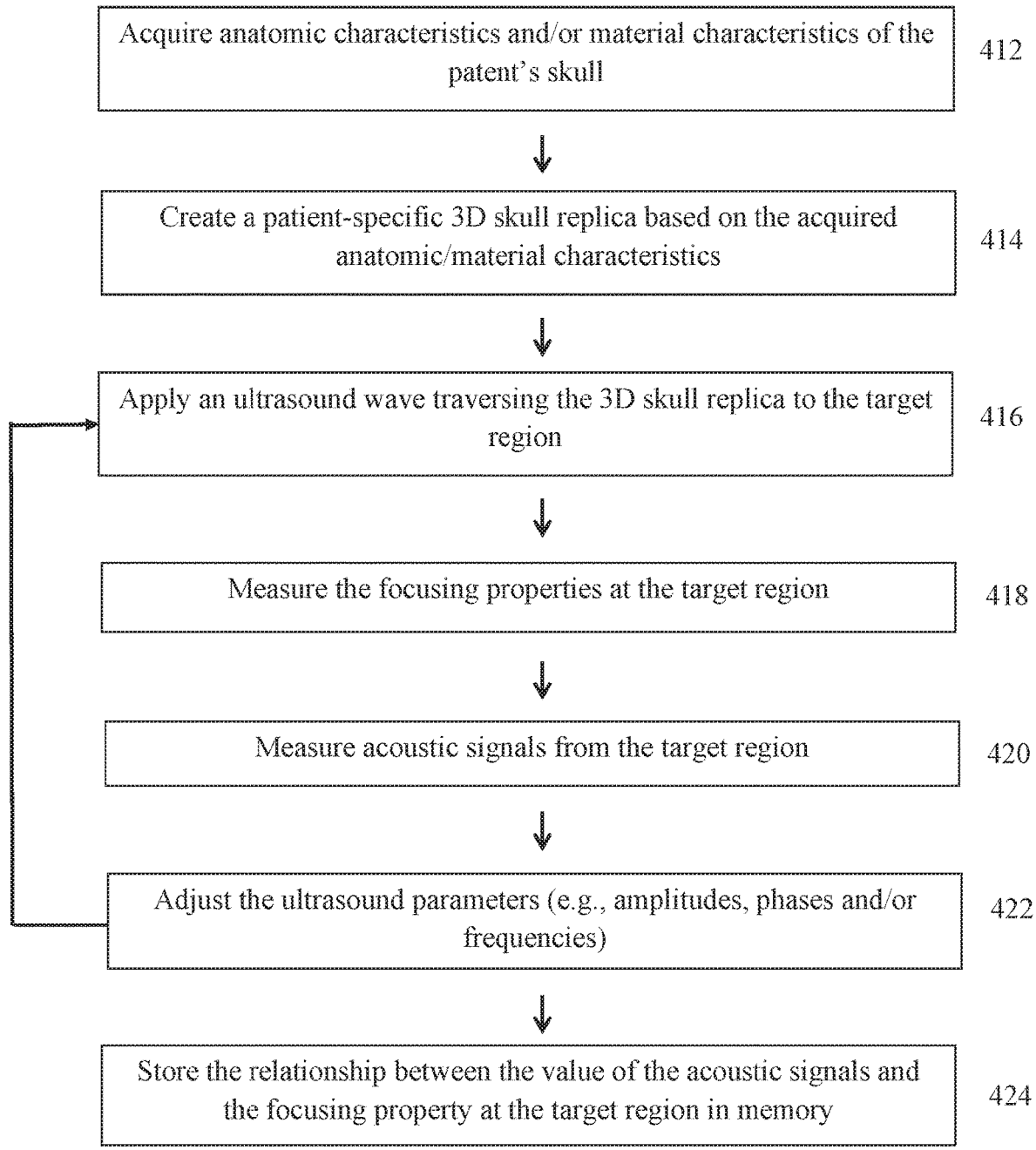
FIG. 4B, is a flow chart illustrating an approach for establishing a relationship between a parameter value of acoustic signals from the target region and the corresponding focusing properties at the target region using a 3D skull replica or an ex-vivo skull in accordance with various embodiments of the present invention.

Alternatively, referring to FIGS. 4A and 4B, the relationship between the parameter value (e.g., the power or amplitude) of the detected acoustic signals and the focusing properties (e.g., the acoustic power or peak acoustic intensity) at the target region may be established using a patient-specific 3D skull replica (or an ex-vivo skull) 402 and a second detector device (e.g., a hydrophone) 404 deployed within the printed skull (or ex-vivo skull) at the target region 101. In one embodiment, prior to treatment, the MRI apparatus 200 and/or other imaging devices (e.g., a computer tomography (CT) device, a positron emission tomography (PET) device, a single-photon emission computed tomography (SPECT) device, or an ultrasonography device) are activated to acquire anatomic characteristics (e.g., type, property, structure, thickness, density, etc.) and/or material characteristics (e.g., energy absorption of the tissue at the employed frequency or the speed of sound) of the patent's skull (in step 412). The patient-specific 3D skull replica 402 may be created based on the acquired anatomic/material characteristics using, for example, 3D printing (in step 414). The 3D skull replica may then be situated in an environment similar to that used to treat the patient; the ultrasound wave may be applied to the target region 101 via traversing the 3D skull replica (in step 416). The second detector device 404 deployed at the target region 101 may be activated to measure the focusing properties (e.g., acoustic power and/or peak acoustic intensity) created by applied ultrasound wave (in step 418). In addition, the detection system 112 may measure the acoustic signals from the target region 101 (in step 420). Again, the ultrasound parameters can be adjusted (in step 422); the transducer is then activated based on the adjusted parameters and the acoustic signals and focusing properties in response to the adjusted parameter values may be measured using the detection system 112 and second detector device 404, respectively. In one embodiment, step 416-422 are repeated until sufficient data has been acquired to reliably establish the relationship between the value of the acoustic signals and the focusing properties at the target region 101 (as depicted in FIG. 3B). Again, the relationship may then be stored in memory accessible to the control 108 (in step 424). Approaches to creating the patient-specific 3D skull replica are provided, for example, in the U.S. patent application Ser. No. 16/132,630, the contents of which are incorporated herein by reference.

Utilizing the established relationship between measurements and one or more focusing properties, a focusing property (e.g., the acoustic power or peak intensity) at the target region may be monitored by inferring it from the measured acoustic signal and/or tissue displacement. Based on the measured acoustic power and/or tissue displacement, the controller 108 may automatically adjust the ultrasound parameter(s) in a closed-loop fashion in order to achieve a desired acoustic pressure. For example, if the measured acoustic power is less than a desired value, the controller 108 may increase the ultrasound power and/or adjust the frequency and/or phase shifts associated with the transducer elements 104 to increase the acoustic power at the target region. Through iterative cycles of measurement and adjustment as ultrasound is reflected from the microbubbles, a high-power ultrasound focus may be reliably generated at the target region 101.

Figure 5:
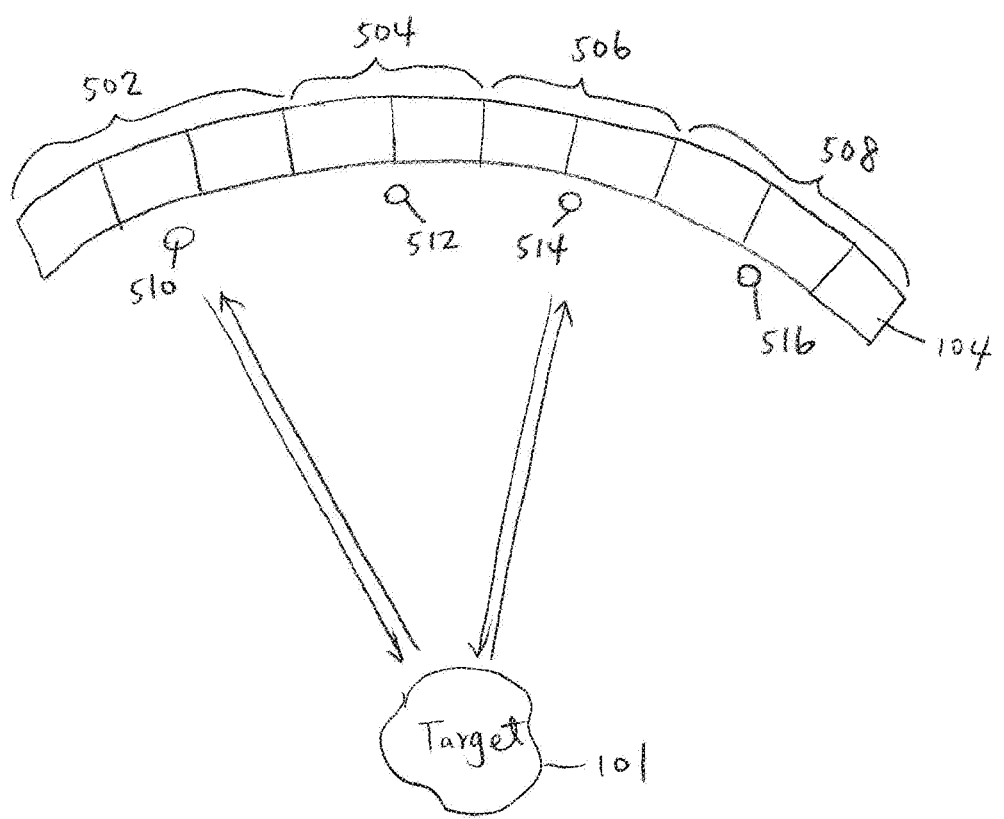
FIG. 5 depicts multiple transducer regions and multiple acoustic-signal detectors for measuring acoustic signals from the target region in accordance with various embodiments of the present invention.

Additionally or alternatively, referring to FIG. 5, the acoustic signals from the target region 101 may be detected by the transducer elements 104 located at different regions 502-508 of the transducer 102 and/or multiple acoustic-signal detectors 510-516 associated with different regions of the transducer 102. By analyzing the relative amplitudes of the reflected acoustic signals received at different regions of the transducer 102, the relative contributions of the energy at the target region 101 from the respective regions of the transducer may be determined. The controller 108 may then adjust the ultrasound parameter values based on the determined relative energy contributions so as to improve the focusing properties at the target region 101, avoid damage to non-target tissue and/or shape the acoustic beam at the target. For example, if the amplitudes of the acoustic signals received at the transducer regions 502, 504 are larger than those received at the transducer regions 506, 508, the transducer regions 502, 504 is contributing more energy at the target region 101 than the transducer regions 506, 508 (in other words, more energy from the transducer regions 506, 508 is absorbed/refracted/reflected on the beam paths before arriving the target region 101). Accordingly, the controller 108 may increase the energy emitted from the transducer regions 506, 508 to compensate for the energy lost along the beam paths to the target 101, thereby improving the acoustic power at the target region 101. Alternatively, the controller 108 may reduce the energy emitted from the transducer regions 506, 508 to avoid overheating the tissue located on the beam paths to the target. This may be beneficial when, for example, the non-target tissue located on the beam paths is an important organ and/or is highly heat-sensitive. In some embodiments, the controller 108 may shape the focus based on the acoustic signals received at different transducer regions. For example, the controller 108 may adjust the transmission phases and amplitude apodization from the transducer regions so as to shape the focus to conform to a specific target shape. Alternatively or additionally, the controller 108 may shape the focus using a physical model that simulates acoustic beams from the transducer regions to the target 101. Approaches to establishing the physical model and using the physical model to perform acoustic simulation are provided in International Patent Publication No. WO 2018/130867 and U.S. Patent Publication No. 2015/0359603, the entire disclosures of which are hereby incorporated herein by reference.

In various embodiments, one or more focusing properties (e.g., the acoustic power) at the target region 101 are estimated based on the spectral signatures of the detected acoustic signals from the microbubbles. This is feasible because different types of cavitation typically have different spectral signatures. For example, at a relatively low acoustic power (e.g., 1-2 Watts above the microbubble-generation threshold), the generated microbubbles undergo oscillation with compression and rarefaction that are equal in magnitude and thus the microbubbles generally remain unruptured (i.e., a "stable cavitation"). The acoustic response of microbubbles is linear at this low acoustic power and the frequency of ultrasound emitted from the microbubbles is the same as or a harmonic of that of the incident ultrasound waves (i.e., the fundamental frequency or a base harmonic frequency). At a higher acoustic power (e.g., more than 10 Watts above the microbubble-generation threshold), the generated microbubbles undergo rarefaction that is greater than compression, which may cause cavitation and a nonlinear acoustic response of the microbubbles. The acoustic signals returned from cavitation events may include frequencies at the fundamental frequency and/or a harmonic, ultra-harmonic, and/or sub-harmonic of the fundamental frequency. This approach may thus involve a mapping between various spectral signatures and their corresponding acoustic powers inducing the cavitation events, which, again, can be straightforwardly established prior to treatment. As used herein, the term "fundamental" frequency or "base harmonic" frequency, $f_0$, refers to the frequency (or temporally varying frequency) of the ultrasound waves/pulses emitted from the transducer array 102; the term "harmonic" refers to an integer number of the fundamental frequency (e.g., $2f_0$, $3f_0$, $4f_0$, etc.); the term "ultra-harmonic" refers to a fractional frequency between two nonzero integer harmonics (e.g., $3f_0/2$, $5f_0/4$, etc.); and the term "sub-harmonic" refers to a fractional number between the fundamental frequency and the first harmonic (e.g., $f_0/2$, $f_0/3$, $f_0/4$, etc.).

Figure 6:
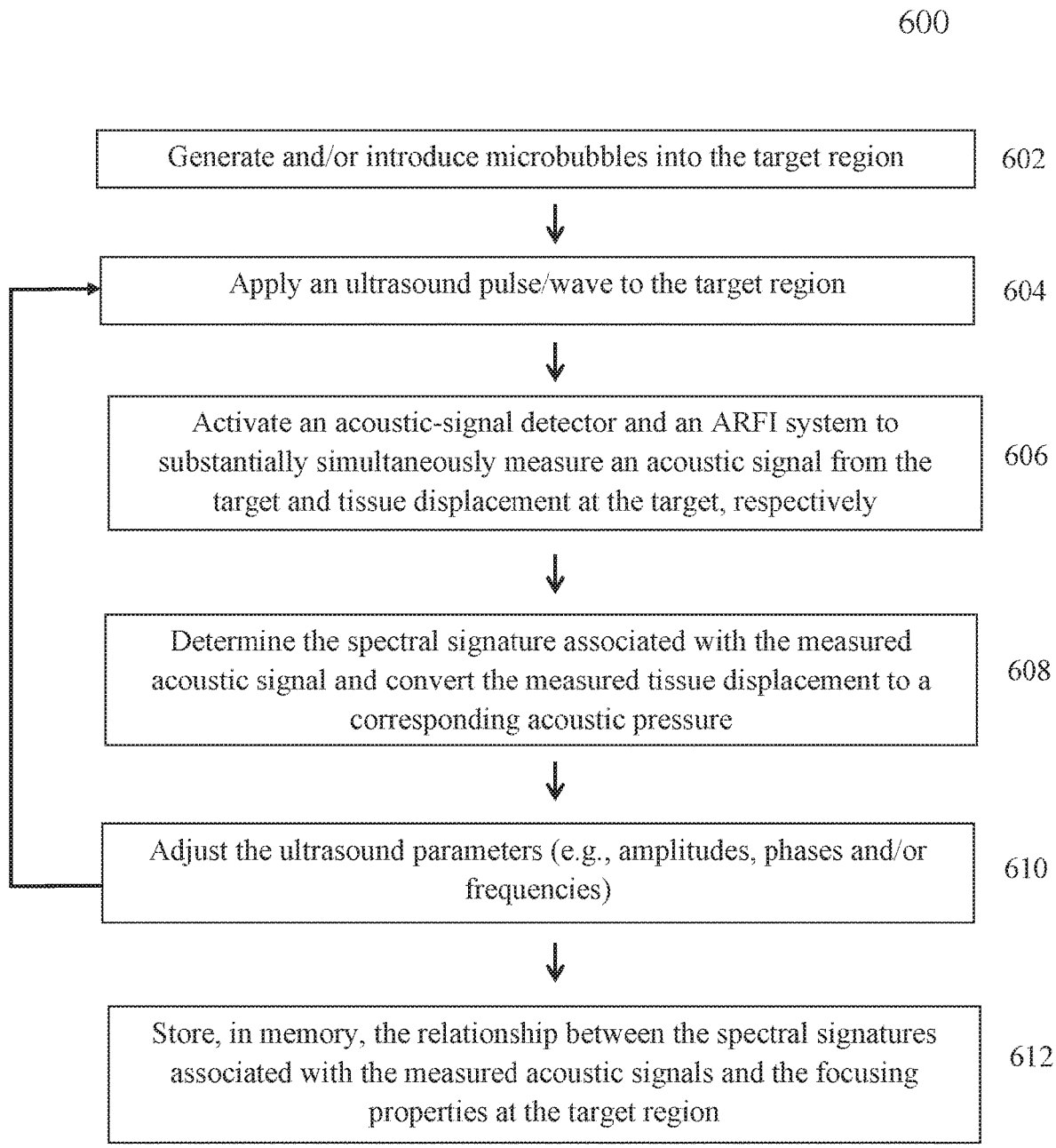
FIG. 6 is a flow chart illustrating an approach for establishing a relationship between spectral signatures of acoustic signals from the target region and the corresponding focusing properties at the target region in accordance with various embodiments of the present invention.

FIG. 6 depicts an exemplary approach 600 for establishing the mapping between the spectral signatures and their corresponding acoustic powers in accordance herewith. In a first step 602, the microbubbles may be generated within and/or introduced into the target region 101. In a second step 604, the transducer elements 104 may apply an ultrasound pulse/wave to the target region. Again, parameter values (e.g., amplitudes, phases, or frequencies) associated with the transducer elements 104 may be estimated empirically and/or using the physical model so as to generate a focus at the target region as described above. In a third step 606, upon application of the ultrasound wave, the acoustic-signal detector 112 (or, in some embodiments, the transducer elements 104) and ARFI system may be activated to substantially simultaneously measure an acoustic signal from the target and tissue displacement at the target, respectively. In a fourth step 608, the measured acoustic signal is then transmitted to the controller 108 for determining the spectral signature associated therewith. In addition, the measured tissue displacement may be converted to a corresponding acoustic pressure based on a known relationship as described above. In a fifth step 610, the ultrasound parameters (e.g., amplitudes, phases, or frequencies) can then be adjusted, and the acoustic signal and tissue displacement in response to the adjusted parameter values are measured. Step 604-610 may be repeated until sufficient data has been acquired to reliably establish the relationship between the spectral signatures of the acoustic signals and the focusing property or properties (e.g., the acoustic power) at the target region 101. Again, the established relationship may then be stored in memory accessible to the controller 108 (in step 612).

Figure 7:
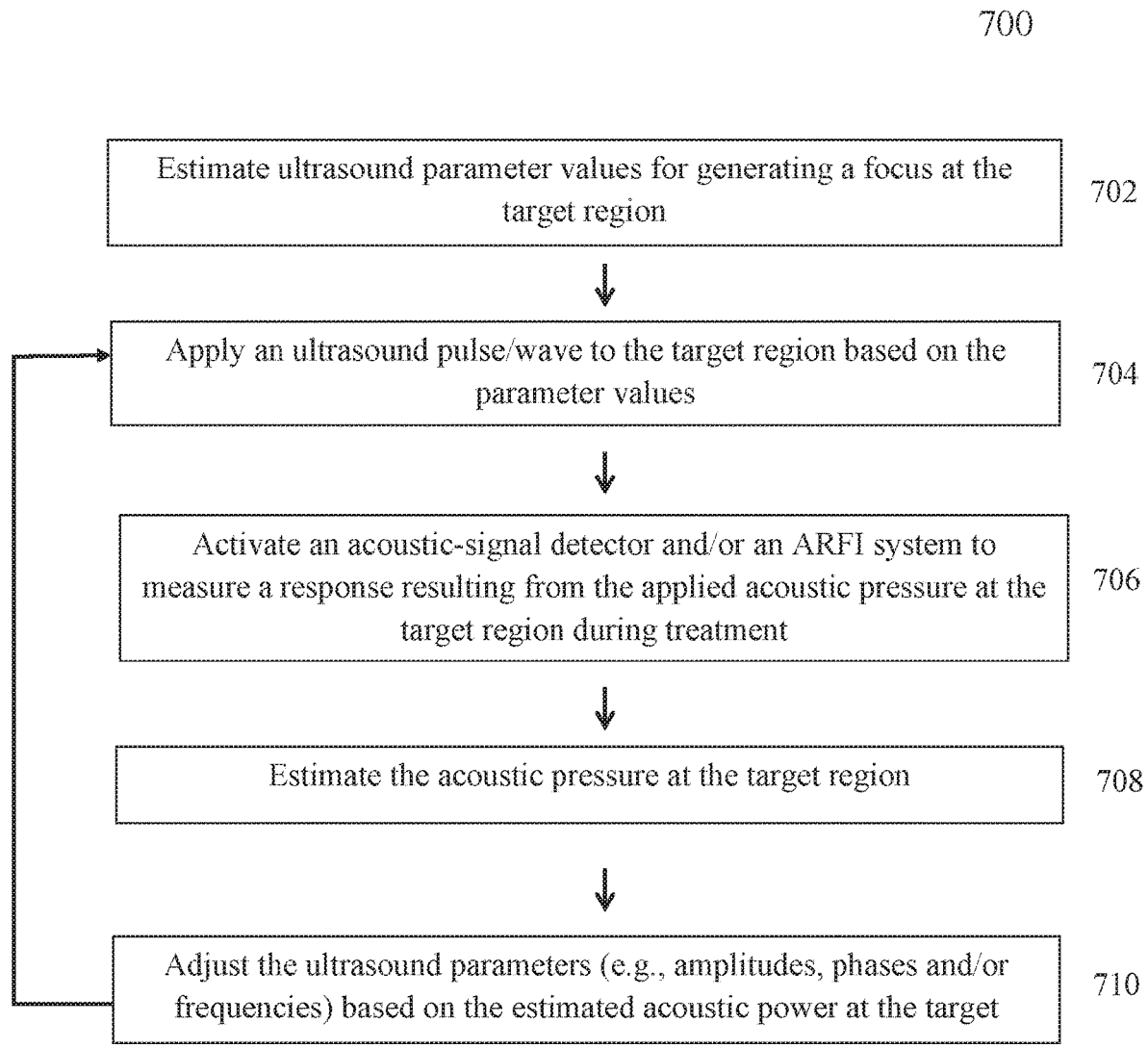
FIG. 7 is a flow chart illustrating an approach for measuring and improving the focusing properties at the target region in real time during treatment in accordance with various embodiments of the present invention.

Once the relationships between the parameter value (or, in some embodiments, the spectral signatures) of the acoustic signals and the focusing properties at the target region are established using, for example, the approaches described in FIGS. 3B, 4B, and 6, the ultrasound focusing properties at the target region 101 may be monitored in real time during a treatment procedure. In particular, acoustic signals from the target region 101 are obtained and, based thereon, one or more parameters (e.g., phase shifts, frequencies and/or amplitudes) of the transducer elements 104 are inferred and may be adjusted in order to improve the focusing properties. FIG. 7 depicts an exemplary approach 700 for measuring and improving the ultrasound focusing properties in accordance herewith. In a first step 702, the ultrasound parameter values are estimated empirically and/or using a physical model to generate a focus at the target region 101 as described above. In a second step 704, the transducer elements 104 are activated based on the estimated parameter values. In a third step 706, the detection system 112 (e.g., the MR-ARFI imaging system and/or an acoustic-signal detector) is employed to measure a response (e.g., a tissue displacement and/or an acoustic signal) resulting from the applied acoustic pressure at the target region 101 during treatment. Optionally, the acoustic pressure may be measured using microbubbles generated within and/or introduced into the target region 101. In a fourth step 708, based on the response measured in step 706, the acoustic pressure at the target region 101 can be estimated. In one implementation, this step involves use of the established relationship between the value (e.g., the power or amplitude) of the detected acoustic signals (and/or the detected tissue displacements) and the corresponding focusing properties (e.g., the acoustic power or peak acoustic intensity) at the target region 101 as described above. Subsequently, the transducer parameter values (e.g., phase shifts, frequencies and/or amplitudes) can be adjusted based on the estimated acoustic power at the target (in step 708). Steps 702-708 may be repeated until the detected ARFI signals and/or acoustic reflection signals are consistent with a desired acoustic pressure.

Figure 8:
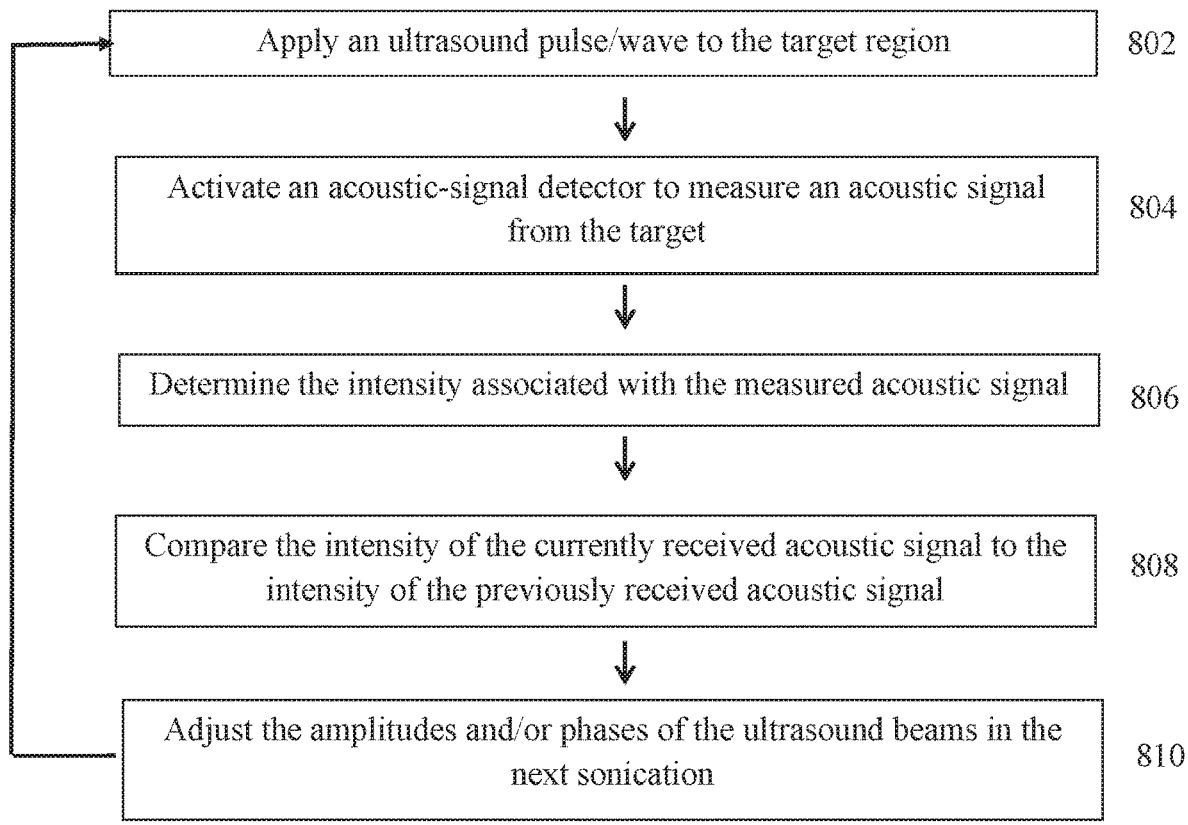
FIG. 8 is a flow chart illustrating an approach for achieving desired focusing properties at the target region without directly measuring the focusing properties at the target region in accordance with various embodiments of the present invention.

In another embodiment, it is not necessary to acquire the focusing properties at the target region in order to achieve a desired power at the target region 101. For example, referring to FIG. 8, the treatment efficiency may be optimized by finding the maximal intensity (or amplitude) of the reflected ultrasound waves, since a higher reflection intensity indicates a higher beam intensity at the focus. Thus, the transducer elements 104 may first apply an ultrasound pulse/wave to the target region 101 (in step 802). The acoustic reflection signal from the target 101 may then be detected using the acoustic-signal detector 112 and/or transducer elements 104 (in step 804). In some embodiments, the measured acoustic signal is transmitted to the controller 108, which determines the intensity associated therewith (in step 806). The controller 108 may compare the intensity of the currently received reflection to the intensity of the previously received reflection (if there is any) (in step 808) and, based on the difference, the controller may adjust the amplitudes and/or phases of the ultrasound beams in the next sonication (in step 810). Again, steps 802-810 can be iterative (that is, the initial parameter values of the transducer elements for the next sonication are determined based on the results of the previous measurements) until the intensity of the reflected acoustic beams reaches a maximum. In some embodiments, the iterative process stops when the difference between the currently measured intensity and the previously measured intensity is below a threshold and/or the number of iterations exceeds a predetermined limit. The threshold may be established, for example, as the value below which no clinical effect is observed.

The goal of a focused-ultrasound lesioning treatment is generally to maximize the energy absorbed at the target while minimizing the exposure of healthy tissue surrounding the target, as well as tissues along the path between transducer and target, to ultrasound. The degree of ultrasound absorption for a propagation length in tissue is a function of frequency, given by: $I=I_0\ e^{-2\alpha f \bar{z}}$, where I represents the acoustic intensity at the target region 101, $I_0$ represents the initial intensity of ultrasound beams emitted from the transducer element, f represents the frequency of the ultrasound (measured in MHz), $\alpha$ represents the pressure absorption coefficient at the relevant frequency range (measured in $cm^{-1} \cdot MHz^{-1}$) and may be acquired from known literature, and z represents a distance that the ultrasound beam propagates through the tissue prior to reaching the target region (which is measured in cm). The higher the product of the greater will be the energy absorption in the target region. Accordingly, in some embodiments, the frequency of the ultrasound is optimized by sequentially sonicating the target region 101 with waves having different "test frequencies" within a test frequency range; for each tested frequency, the acoustic power indicative of energy absorption in the target region 101 is measured using, e.g., an ARFI system. Additionally or alternatively, ultrasound waves at the test frequencies may be transmitted to the microbubbles at the target region; acoustic signals reflected therefrom may be analyzed to acquire the acoustic intensities, I, at the target. Energy absorption at the target can then be inferred from the product $I \cdot \alpha \cdot f$. The test range may span the entire range of frequencies suitable for ultrasound treatment (e.g., in various embodiments, 0.1 MHz to 10 MHz), but is typically a much smaller sub-range thereof in which the optimal frequency is to be expected. Such a sub-range may be determined, e.g., based on a physical model estimating the optimal frequency, the results of simulations, or empirical data acquired for the same target in other patients. The frequencies to be tested may be distributed uniformly or non-uniformly over the test range. In various embodiments, the density of test frequencies increases with proximity to an estimated optimal frequency based on, e.g., prior experience with the same organ or tissue. The test range and the test frequencies therein may be predetermined, or adjusted dynamically during the optimization process. For example, in one embodiment, testing is initially performed at large frequency intervals (e.g., in steps of 20 kHz) over a large test range (e.g., from 0.1 to 1 MHz) to determine a sub-range of frequencies resulting in high energy absorption at the target region 101, and the optimum frequency is thereafter determined within the determined sub-range by testing at smaller intervals (e.g., in steps of 5 kHz). In another embodiment, testing is performed for a subset of predetermined potential test frequencies, each actual test frequency being selected from the set of potential test frequencies based on the results of previous tests or simulations.

Thus, optimizing the ultrasound frequency may involve iteratively setting a test frequency, sonicating the target region 101 at the selected frequency, and quantitatively assessing the resulting acoustic power at the target region 101. Because the acoustic intensity, I, is a function of the acoustic pressure, P, ($I=P^2/Z$, where Z represents the acoustic impedance), the frequency-dependent absorption coefficient of the target tissue can be computed based on the test frequency and its resulting acoustic pressure. In one embodiment, the frequency that has the highest product $I \cdot \alpha \cdot f$ is selected to be the optimal frequency for maximizing the amount of energy absorbed at the target region. In another embodiment, the test frequency that corresponds to the maximal acoustic pressure is determined to be the optimal frequency. In any case, during treatment, the ultrasound transducer 102 is activated in accordance with the determined optimal frequency to treat the target. Although for ease of reference the description herein only refers to assessing the acoustic power at the target region, it should be understood that any suitable experimental technique for measuring a parameter that correlates with energy absorption at the target region 101 in a known and predictable manner may be used and is within the scope of the present invention. For example, MRI thermometry may be employed to measure the temperature increase in the target region 101 resulting from the absorbed energy. Further details about determining the optimal frequency for the ultrasound application are provided, for example, in U.S. Patent Publication No. 2016/0008633, the content of which is incorporated herein by reference.

Although the optimal frequency may maximize the amount of energy absorbed at the target, it may also maximize the exposure of healthy tissue surrounding the target to ultrasound, thereby causing undesired damage thereto. Accordingly, in some embodiments, it is preferable to apply sonications having a frequency corresponding to a lower product $I \cdot \alpha \cdot f$ (compared to that of the optimal frequency) so as to avoid damage to the non-target tissue. This, however, may significantly reduce the amount of energy available at the target region 101. Accordingly, in some embodiments, when the energy absorbed by the target is below a predetermined value that corresponds to the minimally acceptable treatment efficiency, microbubbles are introduced and/or generated at the target region 101 to enhance the treatment efficiency via interaction between the microbubbles and the acoustic beam. The amount of energy absorption at the target, again, can be inferred from the acoustic power or other energy-correlated parameter measured using ARFI, acoustic signals reflected or transmitted from the target 101 and/or other suitable approach. In addition, after administration of the microbubbles for enhancing treatment efficiency, the information characterizing the energy absorption at the target may be updated, and based thereon, the administration profile (e.g., concentration, administered dose, rate or timing) of the microbubbles may be adjusted.

Figure 9A:
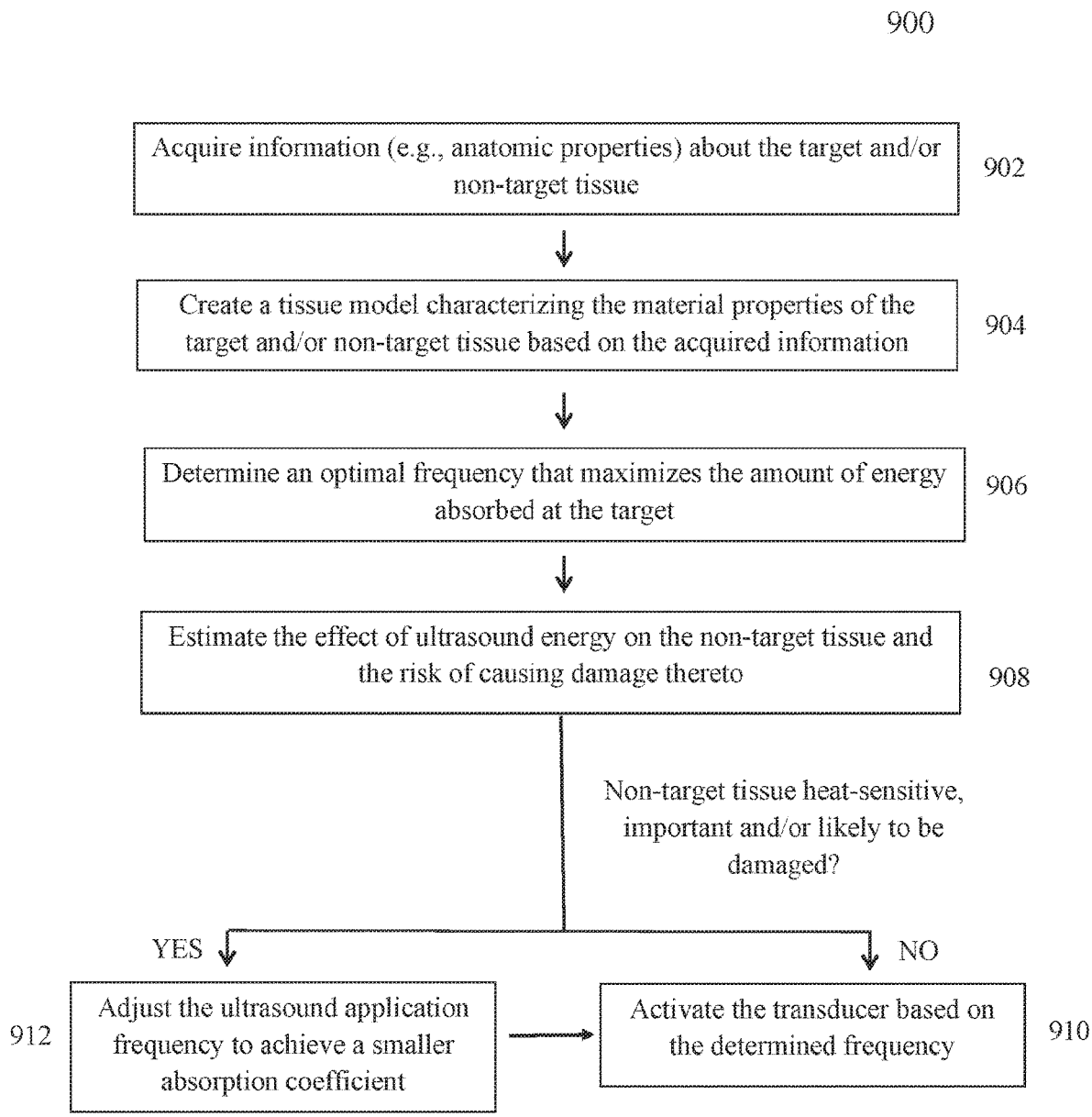
FIG. 9A is a flow chart illustrating an exemplary approach for determining an ultrasound application frequency in a focused-ultrasound treatment in accordance with various embodiments of the present invention.

FIG. 9A depicts an exemplary approach 900 for determining an ultrasound application frequency in a focused-ultrasound treatment in accordance therewith. In a first step 902, information (e.g., anatomic properties) about the target and/or non-target tissue is acquired using an imaging device (e.g., the MRI apparatus 200). Based on the acquired information, a tissue model characterizing the material properties of the target and/or non-target tissue may be created (in a second step 904). Approaches to creating the tissue model are described, for example, in International Application No. PCT/IB2017/001689 (filed on Dec. 13, 2017), the entire disclosure of which is incorporated herein by reference. In a third step 906, an optimal frequency that maximizes the energy absorbed at the target 101 may be determined using the approaches described above. In a fourth step 908, the effect of ultrasound energy on the non-target tissue and the risk of causing damage thereto is estimated based on the tissue model and the determined optimal frequency. If the non-target tissue is highly tolerant of heat and/or can sustain damage without adverse clinical effect (or if the risk of damaging the tissue is low, e.g., less than 20%), the transducer may be activated at the optimal frequency determined in step 806 for treatment (in step 910). If, however, the non-target organ is heat sensitive and/or the risk of damaging it is high (e.g., larger than 50%), the ultrasound application frequency is adjusted to achieve a lower product $I \cdot \alpha \cdot f$ (compared to that of the optimal frequency) so as to avoid damage to the non-target tissue (in step 912). The transducer 102 may be then activated based on the adjusted frequency to commence the treatment procedure (step 910).

Figure 9B:
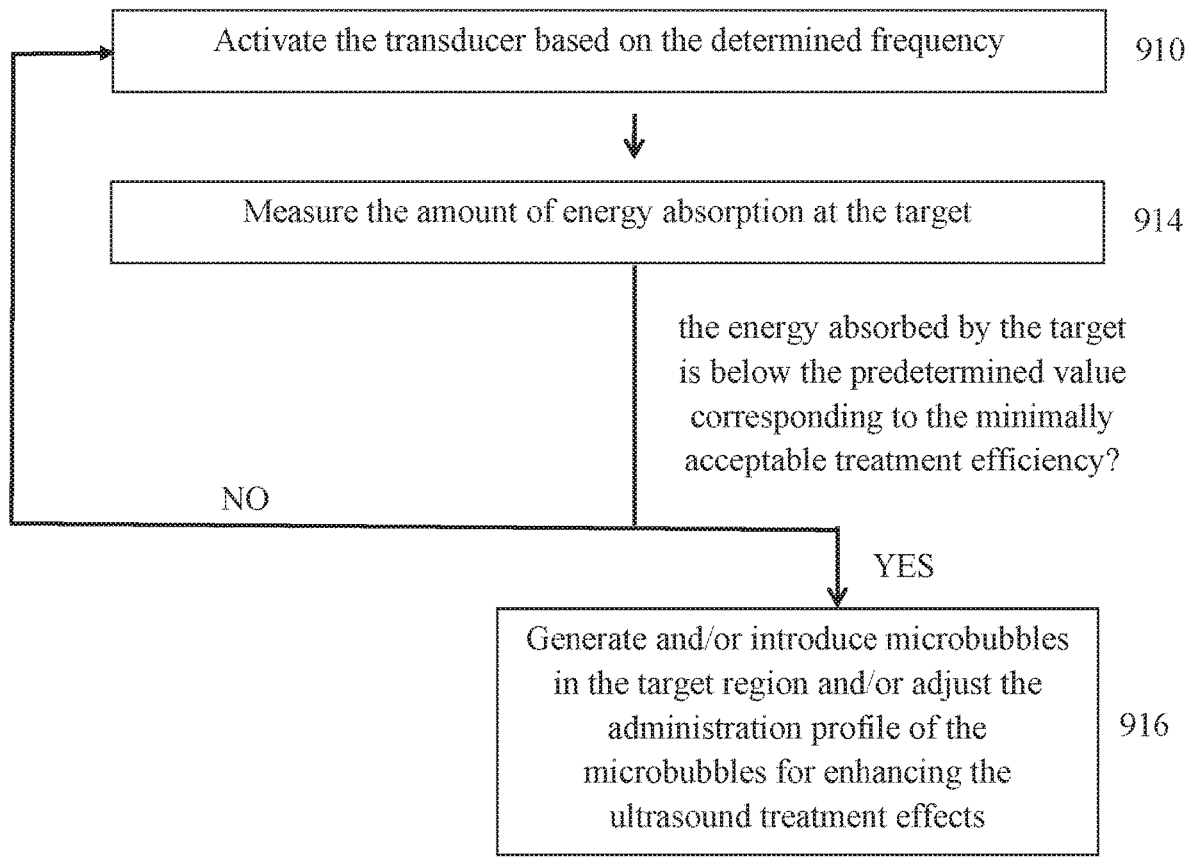
FIG. 9B is a flow chart illustrating an exemplary approach for utilizing microbubbles to enhance treatment effects of the ultrasound procedure in accordance with various embodiments of the present invention.

Referring to FIG. 9B, during treatment, the amount of energy absorption at the target 101 is inferred from the acoustic power or other energy-correlated parameter measured using ARFI, acoustic signals reflected or transmitted from the target 101 and/or other suitable approach as described above (in step 914). If the energy absorbed by the target 101 is below the predetermined value corresponding to the minimally acceptable treatment efficiency, microbubbles may be introduced and/or generated at the target region 101 as described above for enhancing the ultrasound treatment effects (in step 916). The energy absorption at the target may be continuously monitored and updated, and based thereon, the administration profile (e.g., concentration, administered dose, rate or timing) of the microbubbles may be adjusted to improve the focusing properties (in step 818).

Accordingly, various embodiments in the present invention advantageously utilize the detection system 112 to provide closed-loop feedback information (e.g., acoustic power) about the target to an operator or to an automatic controller 108 so as to allow ultrasound parameters to be adjusted (or microbubbles to be introduced in some embodiments) to achieve a desired acoustic power or energy absorption at the target in real time during treatment.

While the examples herein describe the technique with respect to the delivery of ultrasound energy, it should be understood that the ultrasound procedure may be performed in combination with other therapeutic methods, such as radiation therapy or targeted drug delivery. For example, the ultrasound-induced microbubble oscillation/cavitation may disrupt vascular tissue in the target region 101; this allows tissue sensitization to radiation thus reduces the radiation dose needed in radiation therapy while still achieving the desired treatment efficacy. In another treatment scenario, ultrasound-induced microbubble oscillation/cavitation may increase the tissue permeability at the target region (e.g., opening the BBB); this allows a higher dose of therapeutic agent to reach the target tissue, thereby enhancing the therapeutic effect while minimizing systemic toxicity. Approaches to utilizing microbubble oscillation/cavitation to reduce the radiation dose in radiation therapy and increase tissue permeability at the target region 101 are provided, for example, in U.S. patent application Ser. No. 15/637,163 (filed on Jun. 29, 2017) and in International Application No. PCT/IB2018/000811 (filed on Jun. 29, 2018), respectively, the contents of which are incorporated herein by reference.

In addition to or instead of measurements of transmissions from the entire transducer 102, in some embodiments, the above-described approaches can be applied to measurements of transmissions from one or more subsets of the transducers elements 104. In one embodiment, transmissions from several subsets of elements having different spatial arrangements with respect to the target 101 are measured separately; information acquired by analyzing the measurements as described above is used to adjust the transmission power of the subset elements with respect to each other. In some embodiments, the frequencies and/or powers of subset elements can be adjusted to minimize the heating effect on the non-target tissue.

It should be noted although the ultrasound focusing procedure described herein utilizes microbubbles to reflect ultrasound waves, the ultrasound waves may be reflected using other approaches. For example, the administration system 113 may administer emulsions and/or droplets composed of various liquid perfluorocarbon agents into the target region 101 prior to and/or during the treatment. Initial application of the ultrasound pulses may cause the droplets to vaporize into microbubbles, and subsequent application of the ultrasound pulses may be reflected from the microbubbles. The reflections from the target region 101 may be detected and analyzed as described above.

In general, functionality for measuring and improving the focusing properties at the target region 101 in real time during ultrasound treatment, including, for example, estimating ultrasound parameter values for generating a focus at the target region, causing the transducer element 104 to transmit ultrasound pulses/waves to the target region based on the estimated parameter values, activating an acoustic-signal detector and/or an ARFI system to measure an acoustic signal reflected from the target and tissue displacement at the target, respectively, determining a spectral signature and/or an intensity associated with the measured acoustic reflection signal, converting the measured tissue displacement to a corresponding acoustic pressure, comparing the intensity of the currently received acoustic signal to the intensity of the previously received acoustic signal, adjusting the ultrasound parameter values, analyzing imaging data of the target and/or non-target regions acquired using one or more imaging modalities (e.g., ultrasound imaging, MR imaging or a camera), determining the target location, creating a tissue model characterizing the material characteristics of the target/non-target regions based on the imaging data, determining an optimal frequency that maximizes the amount of energy absorbed at the target 101, estimating the effect of ultrasound energy on the non-target tissue and the risk of causing damage thereto, causing a patient-specific 3D skull replica to be created based on the acquired anatomic/material characteristics, causing microbubbles to be generated within and/or introduced into the target region, and/or adjusting the administration profile (e.g., concentration, administered dose, rate or timing) of the microbubbles, as described above, whether integrated within a controller of the ultrasound system 100, and/or the MRI apparatus 200 or provided by a separate external controller or other computational entity or entities, may be structured in one or more modules implemented in hardware, software, or a combination of both. The ultrasound controller 108 and/or MR controller 216 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" or "automatic controller" used herein broadly includes all necessary hardware components and/or software modules utilized to perform any functionality as described above; the controller may include multiple hardware components and/or software modules and the functionality can be spread among different components and/or modules.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for focusing an ultrasound transducer comprising:
   an ultrasound transducer comprising a plurality of transducer elements;
   two or more acoustic-signal detectors for indirectly measuring a focusing property at a target region including an exogenous agent or microbubbles in proximity thereto; and
   a controller configured to:
   (a) cause the ultrasound transducer to transmit ultrasound waves to the target region;
   (b) cause the two or more acoustic-signal detectors to indirectly measure the focusing property by measuring acoustic signals from the exogenous agent or microbubbles from the target region at two or more regions of the transducer elements, wherein the focusing property comprises at least one of an acoustic pressure or a peak acoustic intensity; and
   (c) based at least in part on the indirectly measured focusing property from the target region at the two or more regions of the transducer elements, adjust a parameter value associated with the two or more regions of the transducer elements so as to achieve a target treatment power at the target region, wherein the parameter value comprises at least one of a frequency, a phase, a power level, or an amplitude of a signal driving the two or more regions of the transducer elements.

2. The system of claim 1, wherein at least one of the acoustic-signal detectors is further configured to indirectly measure the focusing property at a non-target region, and the controller is further configured to adjust the parameter value associated with the two or more regions of the transducer elements so as to avoid damage to the non-target tissue.

3. The system of claim 1, further comprising an administration device for introducing the exogenous agent or microbubbles to the target region.

4. The system of claim 1, wherein the controller is further configured to determine the focusing property based at least in part on a value associated with the measured acoustic signals.

5. The system of claim 4, wherein the controller is further configured to:
   establish a relationship between the value associated with the measured acoustic signals and the focusing property; and
   determine the focusing property based at least in part on the relationship.

6. The system of claim 4, wherein the value associated with the measured acoustic signals comprises at least one of an amplitude, a power, a wave pattern or a spectral signature.

7. A system for focusing an ultrasound transducer comprising:
   an ultrasound transducer comprising a plurality of transducer elements;
   a detection system for indirectly measuring a focusing property at a target region, wherein the detection system comprises at least one of an ARFI imaging system or an acoustic-signal detector; and
   a controller configured to:
   (a) cause the ultrasound transducer to transmit ultrasound waves to the target region;
   (b) cause the detection system to indirectly measure the focusing property; and
   (c) based at least in part on the indirectly measured focusing property, adjust a parameter value associated with at least one of the transducer elements so as to achieve a target treatment power at the target region,
   wherein the controller is further configured to adjust the parameter value to (i) cause cavitation of microbubbles at the target region, and (ii) cause the microbubbles, during cavitation, to behave as half-wavelength or quarter-wavelength rigid-sphere reflectors.

8. The system of claim 1, wherein the controller is further configured to cause at least some of the two or more regions of the transducer elements to measure acoustic signals from the exogenous agent or microbubbles.

9. A system for focusing an ultrasound transducer comprising:
   an ultrasound transducer comprising a plurality of transducer elements;
   a detection system for indirectly measuring a focusing property at a target region, wherein the detection system comprises at least one of an ARFI imaging system or an acoustic-signal detector; and
   a controller configured to:
   (a) cause the ultrasound transducer to transmit ultrasound waves to the target region;
   (b) cause the detection system to indirectly measure the focusing property; and (c) based at least in part on the indirectly measured focusing property, adjust a parameter value associated with at least one of the transducer elements so as to achieve a target treatment power at the target region, wherein the controller is further configured to:
compare an amount of energy absorption at the target region, inferred from the indirectly measured focusing property, to a predetermined value; and
upon determining that the amount of energy absorption at the target region is smaller than the predetermined value, cause an administration device to introduce an exogenous agent or microbubbles to the target region.

10. The system of claim 1, wherein the controller is further configured to adjust the power levels associated with the two or more regions of the transducer elements based at least in part on the measured intensities of the acoustic signals so as to compensate for a difference between the intensities of acoustic signals measured at the two or more regions of the transducer elements.

11. The system of claim 1, wherein the controller is further configured to adjust the parameter value associated with the two or more regions of the transducer elements based on an acoustic simulation.

12. The system of claim 11, wherein the controller is further configured to adjust the parameter value associated with the two or more regions of the transducer elements so as to shape an acoustic beam at the target region.

13. The system of claim 1, wherein the controller is further configured to determine energy absorption of tissue at the target region based at least in part on the indirectly measured focusing property.

14. The system of claim 13, wherein the controller is further configured to determine the frequency based at least in part on the energy absorption.

15. The system of claim 1, wherein the controller is further configured to:
(d) transmit second ultrasound waves, based on the adjusted parameter value, to the target region; and
(e) repeat steps (b), (c), (d) until a stopping condition is satisfied.

16. The system of claim 15, wherein the stopping condition is one or more of:
a difference between currently measured focusing property and previously measured focusing property being below a threshold; or
a number of iterations exceeding a predetermined limit.

17. The system of claim 1, wherein:
the ultrasound transducer comprises a plurality of subsets of transducer elements, each of the subsets having different spatial arrangements with respect to the target region; and
the controller is configured to:
cause two or more subsets of the transducer elements to transmit the ultrasound waves to the target region; and
adjust a parameter value associated with the two or more subsets of the transducer elements so as to achieve a target treatment power at the target region.

18. The system of claim 7, wherein the parameter value comprises at least one of a frequency, a phase, a power level, or an amplitude of a signal driving the at least one of the transducer elements.

19. The system of claim 9, wherein the parameter value comprises at least one of a frequency, a phase, a power level, or an amplitude of a signal driving the at least one of the transducer elements.

20. The system of claim 9, wherein the controller is further configured to cause at least some of the transducer elements to measure acoustic signals from the exogenous agent or microbubbles.

* * * * *